United States Patent
Yadidi

(10) Patent No.: US 9,757,395 B2
(45) Date of Patent: Sep. 12, 2017

(54) DRY POWDER INHALER AND METHODS OF USE

(71) Applicant: OtiTopic Inc., Los Angeles, CA (US)

(72) Inventor: Kambiz Yadidi, Los Angeles, CA (US)

(73) Assignee: OTITOPIC INC., Los Angeles, CA (US)

( * ) Notice: Subject to any disclaimer, the term of this patent is extended or adjusted under 35 U.S.C. 154(b) by 157 days.

(21) Appl. No.: 13/791,734

(22) Filed: Mar. 8, 2013

(65) Prior Publication Data

US 2014/0174437 A1    Jun. 26, 2014

Related U.S. Application Data

(60) Provisional application No. 61/740,407, filed on Dec. 20, 2012.

(51) Int. Cl.
```
A61M 16/00    (2006.01)
A61K 31/616   (2006.01)
A61K 9/00     (2006.01)
```

(52) U.S. Cl.
CPC .......... *A61K 31/616* (2013.01); *A61K 9/0075* (2013.01)

(58) Field of Classification Search
CPC .............. A61M 15/00; A61M 15/0091; A61M 15/0065; A61M 2202/064; A61M 15/0021; A61M 15/0001; A61M 15/0002; A61M 15/0003; A61M 15/0004; A61M 15/0005; A61M 15/0066; A61M 15/0085; A61K 9/0075
See application file for complete search history.

(56) References Cited

U.S. PATENT DOCUMENTS

| | | | |
|---|---|---|---|
| 3,906,950 A | 9/1975 | Cocozza | |
| 4,353,365 A | 10/1982 | Hallworth et al. | |
| 4,885,287 A | 12/1989 | Hussain et al. | |
| 4,995,385 A | 2/1991 | Valentini et al. | |
| 5,256,538 A | 10/1993 | Aiken | |
| 5,327,883 A | 7/1994 | Williams et al. | |

(Continued)

FOREIGN PATENT DOCUMENTS

| | | |
|---|---|---|
| CN | 1388762 | 1/2003 |
| CN | 1491109 | 4/2004 |

(Continued)

OTHER PUBLICATIONS

Aspirin Dosage-Drugs, www.drugs.com, Dec. 2011.*

(Continued)

*Primary Examiner* — Todd J Scherbel
*Assistant Examiner* — Victoria Murphy
(74) *Attorney, Agent, or Firm* — Perkins Coie LLP; James W. Hill; Yingli Wang

(57) ABSTRACT

Methods for reducing the risk of a thromboembolic event, and a related drug delivery system are provided. In some embodiments, a dose of acetylsalicylic acid can be provided in powder form to a patient using a dry powder inhaler. The dose can be effective to reduce a risk of a thromboembolic event in a patient. A dry powder inhaler used for the method can have a mouthpiece, a reservoir for receiving the dose of acetylsalicylic acid, and an actuation member for making available the dose of acetylsalicylic acid for inhalation by a patient through the mouthpiece.

15 Claims, 2 Drawing Sheets

(56) References Cited

U.S. PATENT DOCUMENTS

| | | |
|---|---|---|
| 5,506,203 A | 4/1996 | Backstrom et al. |
| 5,518,998 A | 5/1996 | Backstrom et al. |
| 5,639,441 A | 6/1997 | Sievers et al. |
| 5,673,686 A | 10/1997 | Villax et al. |
| 5,750,559 A | 5/1998 | Bianco |
| 5,855,913 A | 1/1999 | Hanes et al. |
| 5,874,064 A | 2/1999 | Edwards et al. |
| 5,875,776 A | 3/1999 | Vaghefi |
| 6,051,256 A | 4/2000 | Platz et al. |
| 6,051,566 A | 4/2000 | Bianco |
| 6,098,620 A * | 8/2000 | Lloyd .................. A61M 15/00 128/200.14 |
| 6,136,295 A | 10/2000 | Edwards et al. |
| 6,136,346 A | 10/2000 | Eljamal et al. |
| 6,187,344 B1 | 2/2001 | Eljamal et al. |
| 6,254,854 B1 | 7/2001 | Edwards et al. |
| 6,284,282 B1 | 9/2001 | Maa et al. |
| 6,309,623 B1 | 10/2001 | Weers et al. |
| 6,358,530 B1 | 3/2002 | Eljamal et al. |
| 6,408,846 B1 | 6/2002 | Ohki et al. |
| 6,423,344 B1 | 7/2002 | Platz et al. |
| 6,455,028 B1 | 9/2002 | Wulffhart et al. |
| 6,503,480 B1 | 1/2003 | Edwards et al. |
| 6,561,186 B2 | 5/2003 | Casper et al. |
| 6,565,885 B1 | 5/2003 | Tarara et al. |
| 6,569,406 B2 | 5/2003 | Stevenson et al. |
| 6,592,904 B2 | 7/2003 | Platz et al. |
| 6,630,169 B1 | 10/2003 | Bot et al. |
| 6,638,495 B2 | 10/2003 | Kabalnov et al. |
| 6,652,837 B1 | 11/2003 | Edwards et al. |
| 6,705,313 B2 | 3/2004 | Niccolai |
| 6,732,732 B2 | 5/2004 | Edwards et al. |
| 6,737,042 B2 | 5/2004 | Rabinowitz et al. |
| 6,766,799 B2 | 7/2004 | Edwards et al. |
| 6,848,197 B2 | 2/2005 | Chen et al. |
| 6,880,555 B1 | 4/2005 | Brunnberg et al. |
| 6,881,398 B2 | 4/2005 | Myrman et al. |
| 6,884,794 B2 | 4/2005 | Staniforth et al. |
| 6,893,657 B2 | 5/2005 | Roser et al. |
| 6,979,437 B2 | 12/2005 | Bartus et al. |
| 6,994,842 B2 | 2/2006 | Lee et al. |
| 6,998,137 B2 | 2/2006 | Shih et al. |
| 7,025,059 B2 | 4/2006 | Pera |
| 7,089,934 B2 | 8/2006 | Staniforth et al. |
| 7,146,978 B2 | 12/2006 | Edwards et al. |
| 7,189,750 B2 | 3/2007 | Assaf et al. |
| 7,201,929 B1 * | 4/2007 | Finkelstein .................. 424/754 |
| 7,205,343 B2 | 4/2007 | Dellamary et al. |
| 7,267,813 B2 | 9/2007 | Watanabe et al. |
| 7,278,425 B2 | 10/2007 | Edwards et al. |
| 7,284,553 B2 | 10/2007 | Hochrainer |
| 7,306,787 B2 | 12/2007 | Tarara et al. |
| 7,405,207 B2 | 7/2008 | Leonard et al. |
| 7,431,916 B2 | 10/2008 | Nilsson et al. |
| 7,435,720 B2 | 10/2008 | Quay et al. |
| 7,516,741 B2 | 4/2009 | Glusker et al. |
| 7,521,068 B2 | 4/2009 | Bosch et al. |
| 7,534,914 B2 | 5/2009 | Koike et al. |
| 7,541,022 B2 | 6/2009 | Staniforth et al. |
| 7,556,035 B2 | 7/2009 | Young et al. |
| 7,556,798 B2 | 7/2009 | Edwards et al. |
| 7,559,325 B2 | 7/2009 | Dunkley et al. |
| 7,628,978 B2 | 12/2009 | Weers et al. |
| 7,651,770 B2 | 1/2010 | Berkland et al. |
| 7,669,596 B2 | 3/2010 | Alston |
| 7,682,614 B2 | 3/2010 | Strober et al. |
| 7,744,906 B2 | 6/2010 | Coates |
| 7,790,145 B2 | 9/2010 | Weers et al. |
| 7,806,117 B2 | 10/2010 | Tsutsui |
| 7,878,193 B2 | 2/2011 | Kladders et al. |
| 7,919,119 B2 | 4/2011 | Straub et al. |
| 7,954,491 B2 | 6/2011 | Hrkach |
| 8,069,851 B2 | 12/2011 | Dunkley et al. |
| 8,075,919 B2 | 12/2011 | Brown et al. |
| 8,114,438 B2 | 2/2012 | Pipkin et al. |
| 8,168,223 B1 | 5/2012 | Tarara et al. |
| 8,173,168 B2 | 5/2012 | Platz et al. |
| 8,201,555 B2 | 6/2012 | Chawla |
| 8,236,786 B2 | 8/2012 | Finch et al. |
| 8,246,934 B2 | 8/2012 | Weers et al. |
| 8,530,463 B2 | 9/2013 | Cartt et al. |
| 8,561,609 B2 | 10/2013 | Donovan et al. |
| 8,623,419 B2 | 1/2014 | Malakhov et al. |
| 8,771,744 B2 | 7/2014 | Ruecroft et al. |
| 8,790,648 B2 | 7/2014 | Tocker et al. |
| 8,795,634 B2 | 8/2014 | Illum et al. |
| 8,940,683 B2 | 1/2015 | Levitt |
| 8,985,102 B2 | 3/2015 | Hodson et al. |
| 8,997,799 B2 | 4/2015 | Hodson et al. |
| 9,051,302 B2 | 6/2015 | Winssinger et al. |
| 9,061,352 B2 | 6/2015 | Lipp et al. |
| 9,085,632 B2 | 7/2015 | Coates et al. |
| 9,101,539 B2 | 8/2015 | Nagata et al. |
| 9,125,999 B2 | 9/2015 | Rolfs et al. |
| 9,138,407 B2 | 9/2015 | Caponetti et al. |
| 2002/0025917 A1 | 2/2002 | Pappalardo |
| 2002/0158150 A1 * | 10/2002 | Matsugi ............ A61M 15/0065 239/418 |
| 2003/0176421 A1 | 9/2003 | Watson et al. |
| 2003/0186843 A1 | 10/2003 | Staniforth et al. |
| 2003/0232019 A1 | 12/2003 | Basu et al. |
| 2004/0049022 A1 | 3/2004 | Nyce et al. |
| 2004/0092470 A1 | 5/2004 | Leonard et al. |
| 2004/0105821 A1 | 6/2004 | Bernstein et al. |
| 2004/0206350 A1 | 10/2004 | Alston et al. |
| 2005/0000518 A1 | 1/2005 | Dunkley et al. |
| 2005/0004079 A1 | 1/2005 | Benjamin et al. |
| 2005/0084528 A1 | 4/2005 | Saeed et al. |
| 2005/0148555 A1 | 7/2005 | Gupta et al. |
| 2005/0180926 A1 | 8/2005 | Lecourt et al. |
| 2005/0249697 A1 | 11/2005 | Uhrich et al. |
| 2006/0002995 A1 | 1/2006 | Harwigsson |
| 2006/0030550 A1 | 2/2006 | Lithgow et al. |
| 2006/0257987 A1 | 11/2006 | Gonzalez Valcarcel et al. |
| 2006/0293217 A1 | 12/2006 | Barker et al. |
| 2007/0021382 A1 | 1/2007 | Assaf et al. |
| 2007/0072939 A1 | 3/2007 | Kupper |
| 2007/0116761 A1 | 5/2007 | Desai et al. |
| 2007/0123571 A1 | 5/2007 | Raj et al. |
| 2007/0178166 A1 | 8/2007 | Bernstein et al. |
| 2007/0232575 A1 | 10/2007 | Baulieu et al. |
| 2008/0066741 A1 | 3/2008 | LeMajieu et al. |
| 2008/0127972 A1 | 6/2008 | Morton |
| 2008/0226736 A1 | 9/2008 | Caponetti et al. |
| 2008/0306033 A1 | 12/2008 | Franzone et al. |
| 2009/0011030 A1 | 1/2009 | Jouhikainen et al. |
| 2009/0110679 A1 | 4/2009 | Li et al. |
| 2009/0136561 A1 | 5/2009 | Von Rechenberg et al. |
| 2009/0220435 A1 | 9/2009 | Quay et al. |
| 2009/0308392 A1 | 12/2009 | Smutney et al. |
| 2009/0312380 A1 | 12/2009 | Becker |
| 2010/0132705 A1 | 6/2010 | De Vos |
| 2010/0158819 A1 | 6/2010 | Kligerman et al. |
| 2010/0168710 A1 | 7/2010 | Braithwaite |
| 2010/0234442 A1 | 9/2010 | Duarte-Vazquez et al. |
| 2010/0242960 A1 | 9/2010 | Zangerle |
| 2010/0258118 A1 | 10/2010 | Morton |
| 2010/0316724 A1 | 12/2010 | Whitfield et al. |
| 2010/0319694 A1 | 12/2010 | Cook et al. |
| 2011/0112134 A1 | 5/2011 | Hutchinson et al. |
| 2011/0142914 A1 | 6/2011 | Persaud et al. |
| 2011/0146678 A1 | 6/2011 | Ruecroft et al. |
| 2011/0166133 A1 | 7/2011 | Albaugh et al. |
| 2011/0189106 A1 | 8/2011 | Danzig et al. |
| 2011/0250130 A1 | 10/2011 | Benatuil et al. |
| 2011/0263610 A1 | 10/2011 | Wan et al. |
| 2011/0277752 A1 | 11/2011 | Cheu et al. |
| 2012/0017892 A1 | 1/2012 | Ludwig |
| 2012/0046251 A1 | 2/2012 | Schaeffer et al. |
| 2012/0064126 A1 | 3/2012 | Sung et al. |
| 2012/0125325 A1 | 5/2012 | Bannister et al. |
| 2012/0132203 A1 | 5/2012 | Hodson et al. |
| 2012/0145150 A1 | 6/2012 | Donovan et al. |
| 2012/0152245 A1 | 6/2012 | Rolfs et al. |

(56) References Cited

U.S. PATENT DOCUMENTS

| | | | |
|---|---|---|---|
| 2012/0263680 A1 | 10/2012 | Lander et al. | |
| 2012/0276193 A1 | 11/2012 | Graversen et al. | |
| 2012/0291780 A1* | 11/2012 | Donovan et al. | 128/203.15 |
| 2012/0308566 A1 | 12/2012 | Martin et al. | |
| 2012/0309809 A1 | 12/2012 | Green et al. | |
| 2013/0004969 A1 | 1/2013 | Peschon et al. | |
| 2013/0028942 A1 | 1/2013 | Surber et al. | |
| 2013/0316001 A1 | 11/2013 | Popov et al. | |
| 2014/0065219 A1 | 3/2014 | Bosch et al. | |
| 2014/0079784 A1 | 3/2014 | Burnier et al. | |
| 2014/0174437 A1 | 6/2014 | Yadidi | |
| 2014/0174440 A1 | 6/2014 | Yadidi | |
| 2014/0213560 A1 | 7/2014 | Vakkalanka | |
| 2014/0234330 A1 | 8/2014 | Budelsky et al. | |
| 2014/0239525 A1 | 8/2014 | McConville et al. | |
| 2014/0242174 A1 | 8/2014 | Walker | |
| 2014/0322238 A1 | 10/2014 | Budelsky et al. | |
| 2014/0322328 A1 | 10/2014 | Yadidi | |
| 2014/0364837 A1 | 12/2014 | Boyes et al. | |
| 2015/0005230 A1 | 1/2015 | Eliasof | |
| 2015/0045332 A1 | 2/2015 | Swenson | |
| 2015/0050713 A1 | 2/2015 | Malakhov et al. | |
| 2015/0059746 A1 | 3/2015 | Green | |
| 2015/0093338 A1 | 4/2015 | Farber | |
| 2015/0132386 A1 | 5/2015 | Heng et al. | |
| 2015/0136130 A1 | 5/2015 | Dehaan et al. | |
| 2015/0224129 A1 | 8/2015 | Trottein et al. | |
| 2015/0239866 A1 | 8/2015 | Machacek et al. | |
| 2015/0239966 A1 | 8/2015 | Baciu et al. | |
| 2015/0239987 A1 | 8/2015 | Liang et al. | |
| 2015/0284381 A1 | 10/2015 | Andresen et al. | |
| 2015/0320694 A1 | 11/2015 | Gu et al. | |
| 2015/0322070 A1 | 11/2015 | Rao et al. | |

FOREIGN PATENT DOCUMENTS

| | | |
|---|---|---|
| CN | 102058886 A1 | 5/2011 |
| EP | 1177805 | 2/2002 |
| EP | 1177805 A1 | 2/2002 |
| EP | 1238680 | 9/2002 |
| EP | 1350511 | 10/2003 |
| EP | 1814521 | 8/2007 |
| EP | 1350511 | 9/2008 |
| JP | 2002255814 | 9/2002 |
| JP | 2003525081 | 1/2005 |
| WO | 9511666 | 5/1995 |
| WO | 0027359 A1 | 5/2000 |
| WO | WO-00/27359 | 5/2000 |
| WO | 03047598 A1 | 6/2003 |
| WO | 03047628 A1 | 6/2003 |
| WO | 2005040163 A1 | 5/2005 |
| WO | 2005041886 A2 | 5/2005 |
| WO | 2006017354 A1 | 2/2006 |
| WO | 2007072503 A2 | 6/2007 |
| WO | WO-2009/089822 A2 | 7/2009 |
| WO | WO-2012/061902 | 5/2012 |
| WO | 2012107364 A1 | 8/2012 |
| WO | 2012107765 A2 | 8/2012 |
| WO | 2013004999 A1 | 1/2013 |
| WO | 2014131851 A1 | 9/2014 |
| WO | 2014155103 A1 | 10/2014 |
| WO | 2015002703 A1 | 1/2015 |
| WO | 2015011244 A1 | 1/2015 |
| WO | 2015148415 A2 | 1/2015 |
| WO | 2015054574 A1 | 4/2015 |
| WO | 2015127315 A1 | 8/2015 |
| WO | 2015153838 A1 | 10/2015 |
| WO | 2015155544 A1 | 10/2015 |

OTHER PUBLICATIONS

Hovens et al., Aspirin in the prevention and treatment of venous thromboembolism, Journal of Thrombosis and Haemostasis, 2006, 4: 470-5.*

Keller, Developments and trends in pulmonary drug delivery, Chemistry today, 1998.*
Miser, Appropriate aspirin use for primary prevention of cardiovascular disease, Editorials: controversies in family medicine, 2011.*
Geller, et al., "Development of an Inhaled Dry-Powder Formulation of Tobramycin Using PlumoSphere Technology," J Aerosol Med Pulm Drug Deliv, Aug. 2011, 24(4), pp. 175-182.
Hadinoto et al., "Drug Release Study of Large Hollow Nanoparticulate Aggregates Carrier Particles for Pulmonary Delivery," International Journal of Pharmaceutics 341 (2007) 195-206.
Hovione—Particle Design Technologies, <http://www.hovione.com/pd/particledesigntechnologies.asp>, visited Aug. 2013.
Hovione TwinCaps Dry Powder Inhaler, <http://www.hovione.com/twincaps/twincaps.asp>, visited Aug. 2013.
Kim, et al., "Airway Responsiveness to Inhaled Aspirin is Influenced by Airway Hyperresponsiveness in Asthmatic Patients," Korean J Intern Med, Sep. 2010; 25(3): 309-316.
Phillips et al., "Inhaled Lysine-Aspirin as a Bronchoprovocation Procedure in Aspirin-Sensitive Asthma: its Repeatability, Absence of a Late-Phase Reaction, and the Role of Histamine," J Allergy Clin Immunol, Aug. 1989; 84(2):232-41.
Press release by Activaero GmbH, Dec. 19, 2006, <http://www.pharmaloco.com/news_detail/Activaero+and+Group+of+Resaerchers+Receive+Grant+for+Develop/14009/index.html>.
Sestini et al., "Different Effects of Inhaled Aspirin-like Drugs on Allergen-Induced Early and Late Asthmatic Responses," Am J Respir Crit Care Med, Apr. 1, 1999 vol. 159 No. 4 1228-1233.
Sestini, et al., "Protective Effect of Inhaled Lysine Acetylsalicylate on Allergen-Induced Early and Late Asthmatic Reactions," J Allergy Clin Immunol, 1997 vol. 100, pp. 71-77.
Soleti et al., "Aspirin Inhalation Treatment for COPD Patients: Preliminary Studies on PK and Inflammatory Biomarkers," Thematic Poster Session, P825, Drug delivery and pharmacokinetics I, Sep. 25, 2011, p. 138s.
Iwamoto, "Gastrointestinal and Hepatic First-Pass Metabolism of Aspirin in Rats," J Pharm Pharmacol. Mar. 1982; 34(3), pp. 176-180.
Fehri, et al., "Bioavailability of Acetylsalicylic Acid Administered Orally or Rectally in the Rabbit," J. Pharma Belg, 1989, vol. 44, No. 1, pp. 5-10.
Jaffe, et al., "Recovery of Endothelial Cell Prostacyclin Production after Inhibition by Low Doses of Aspirin," The American Society for Clinical Investigation, Inc., Mar. 1979, vol. 63, pp. 532-535.
"Physicians' Health Study I," <http://phs.bwh.harvard.edu/phs1.htm>, Mar. 2009.
ATT Collaboration, "Aspirin in the Primary and Secondary Prevention of Vascular Disease: Collaborative Meta-Analysis of Individual Participant Data from Randomised Trials," The Lancet, 2009, 373:1849-1860.
Kurth, et al., "Inhibition of Clinical Benefits of Aspirin on First Myocardial Infarction by Nonsteroidal Antiinflammatory Drugs," Circulation, 2003, 108:1191-1195.
Christen, et al., "Low-dose Aspirin and Risk of Cataract and Subtypes in a Randomized Trial of U.S. Physicians" Ophthalmic Epidemiology, 1998, vol. 5, No. 3, pp. 133-142.
The Dutch TIA Trial Study Group, "A Comparison of Two Doses of Aspirin (30 mg vs. 283 mg a day) in Patients After a Transient Ischemic Attack or Minor Ischemic Stroke," The New England Journal of Medicine, 1991, vol. 325, No. 18, pp. 1261-1266.
Boysen, et al., "Danish Very-low-dose Aspirin After Carotid Endarterectomy Trial," Stroke, 1988, 19:1211-1215.
Algra, et al., "Aspirin at Any Dose Above 30 mg Offers Only Modest Protection After Cerebral Ischaemia," J of Neurology, Neurosurgery & Psychiatry, 1996, 60:197-199.
Chew, et al., "The Role of Particle Properties in Pharmaceutical Powder Inhalation Formulations," Journal of Aerosol Medicine, 2002, vol. 15, No. 3, pp. 325-330.
Sung, et al., "Nanoparticles for Drug Delivery to the Lungs," Trends in Biotechnology, 2007, vol. 25, No. 12.
"Aspirin", Martindale: The Complete Drug Reference, 33rd ed., 2002 Pharmaceutical press, pp. 14-18.
Roth, et al., "Aspirin, Platelets, and Thrombosis: Theory and Practice," Blood, Feb. 15, 1994, vol. 83, No. 4, pp. 885-898.

(56) References Cited

OTHER PUBLICATIONS

"Internal Analgesic: Antipyretic, and Antirheumatic Drug Products for Over-The-Counter Human Use: Final Rule for Professional Labeling of Aspirin, Buffered Aspirin, and Aspirin in Combination with Antacid Drug Products," Federal Register, Oct. 23, 1998, vol. 63, No. 205, pp. 56802-56819.

Rocca, et al., "Variability in the Responsiveness to Low-Dose Aspirin: Pharmacological and Disease-Related Mechanisms," Thrombosis, 2012, 11 pages.

Awa, et al., "Prediction of time-dependent interaction of aspirin with ibuprofen using a pharmacokinetic/pharmacodynamics model," Journal of Clinical Pharmacy and Therapeutics, 2012, vol. 37, pp. 469-474.

Hadinoto, et al., "Dry powder aerosol delivery of large hollow nanoparticulate aggregates as prospective carriers of nanoparticulate drugs: Effects of phospholipids," International Journal of Pharmaceuticals, Oct. 2006. 33: 187-198.

Hadinoto, et al. "Drug Release Study of Large Hollow Nanoparticulate Aggregates Carrier Particles for Pulmonary Delivery", International Journal of Pharmaceutics (2007), 341(1-2), 195-206.

Kupczyk, et al. "Lipoxin A4 Generation is Decreased in Aspirin-Sensitive Patients in Lysine-Aspirin Nasal Challenge in Vivo Model", Allergy (Oxford, United Kingdom) (2009), 64(12), 1746-1752.

Hadinoto, et al. "Drug release study of large hollow nanoparticulate aggregates carrier particles for pulmonary delivery" International Journal of Pharmaceutics, Elsevier BV, NL, vol. 341, No. 1-2, Jul. 24, 2007 (Jul. 24, 2007), pp. 195-206.

European Search Report dated Jul. 18, 2016 corresponding to European Application No. 13864747.4; 6 pages.

International Search Report dated Jun. 11, 2013 from corresponding PCT Application No. PCT/US2013/032597; 2 pages.

Written Opinion dated Jun. 11, 2013 from corresponding PCT Application No. PCT/US2013/032597; 5 pages.

\* cited by examiner

DRY POWDER INHALER AND METHODS OF USE

CROSS-REFERENCE TO RELATED APPLICATIONS

This application claims the benefit of U.S. Provisional Application No. 61/740,407, filed Dec. 20, 2012, the entirety of which is incorporated herein by reference.

FIELD

The subject technology relates generally to apparatuses and methods for delivery of substances, e.g., delivery of medication to the lungs using by inhalation for treating disease.

SUMMARY

An aspect of at least one embodiment disclosed herein includes the recognition of a need for improved apparatuses and methods for delivery of drugs for treating disease that utilize a dosage that is effective to reduce a risk of a thromboembolic event in a patient, lower than traditional dosages, and administered using a more direct delivery mechanism to the systemic blood stream.

Thromboembolic Symptoms and Events

A thromboembolic event, such as myocardial infarction, deep venous thrombosis, pulmonary embolism, thrombotic stroke, etc., can present with certain symptoms that allow a patient or clinician to provide an initial therapy or treatment for the event. In some situations, a baby aspirin (81 mg) or a regular aspirin (330 mg) may be orally administered in order to provide an initial treatment for the patient.

According to some embodiments disclosed herein is the realization that this treatment may not act as quickly as necessary to provide a sufficient therapeutic effect and therefore, may lead to a less preferred outcome. Thus, in some embodiments, a drug delivery system and related methods are disclosed that provide an accelerated and more efficient pathway and treatment for reducing the risk of a thromboembolic event and/or providing treatment for a thromboembolic event. For example, some embodiments provide systems and methods of administering a nonsteroidal anti-inflammatory drug ("NSAID") by inhalation, such as by a dry powder inhaler ("DPI") or a metered dose inhaler ("MDI").

Delivery Mechanisms for Drugs

Drugs can be administered orally in different ways, such as liquids, capsules, tablets, or chewable tablets. The oral route is used most often because it is the most convenient, safest, and least expensive. However, oral drug delivery has limitations because of the way a drug typically moves through the digestive tract.

For example, when a drug is administered orally, it is absorbed in the mouth, stomach, and the small intestine. Before the drug enters the bloodstream, it must pass through the intestinal wall and travels to the liver. While passing through the intestinal wall and liver, the drug is metabolized, which can decrease the amount of the drug that actually reaches the bloodstream. The metabolism of the drug reduces the bioavailability of the drug and is often termed the "first pass effect." The fraction of the drug lost during due to the first pass effect is generally determined by absorption in the liver and gut wall, and gastrointestinal lumen enzymes, gut wall enzymes, bacterial enzymes, and hepatic (liver) enzymes.

Generally, the first pass effect on aspirin significantly reduces the bioavailability of the administered dosage. For example, due to the acidic conditions in the stomach, aspirin is absorbed in the stomach and the upper small intestine. After being absorbed, aspirin is metabolized to acetic acid and salicylate. When taken orally, generally only about one to two-thirds of the dose of aspirin is bioavailable due to the first pass effect.

For example, in Iwamoto K., GASTROINTESTINAL AND HEPATIC FIRST-PASS METABOLISM OF ASPIRIN IN RATS, J Pharm Pharmacol. 1982 March; 34(3), pp. 176-80, the entirety of which is incorporated herein by reference, the study examines the absorption of aspirin in four male subjects following an oral solution of 650 mg. As stated in the study report, "the absorption process appeared to follow first-order kinetics, with a half-life ranging from 4.5 to 16.0 min. between subjects. Comparison of the area under the aspirin plasma concentration-time curve following intravenous and oral routes indicated that only 68% of the dose reached the peripheral circulation intact."

The applicant has determined that even drugs that are administered by inhalation undergo a first pass effect. For drug administration by inhalation, smaller particles proceed via a nasal route, down the windpipe (trachea) and into the lungs. The size of the particles can be determinative of the overall efficacy of the treatment. Once inside the lungs, these particles are absorbed into the bloodstream.

Few drugs are administered by inhalation because the dosage of an inhaled drug, as well as the delivery timing, can often be difficult to measure. Usually, this method is used to administer drugs that act specifically on the lungs, such as aerosolized antiasthmatic drugs in metered-dose containers, and to administer gases used for general anesthesia.

Pharmacokinetics of Aspirin

Aspirin is the acetylated form of salicylic acid, and the active chemical in aspirin is called acetylsalicylic acid (ASA). Aspirin is used by millions of people to achieve desirable effects, and by many people, aspirin is used daily in doses of 81 mg (i.e., a baby aspirin). The principal effect of aspirin is to impair the function of cyclooxygenase enzymes (specifically, COX1 and COX2 enzymes).

By inhibiting COX1, aspirin can irreversibly inhibit platelet aggregation, which decreases the risk of blood clots. Additionally, the impairment of the COX2 enzyme can reduce inflammation, stiffness, and pain in the body by inhibiting prostaglandins and thromboxanes. As such, individuals at high risk for heart attack, stroke, or with inflammation often take aspirin to address symptoms and effects of these conditions. As noted, aspirin can effectively reduce the likelihood of such myocardial events and reduce pain and inflammation with a dose as small as 81 mg. However, due at least in part to its inhibition of COX1, aspirin can increase the risk of bleeding and cause damage to organs such as the stomach and intestines, which can be painful.

Dry Powder Inhaler Technology

As stated above, the oral delivery of aspirin may create a risk of damage to the stomach wall leading to pain, indigestion and a high risk of bleeding. Further, according to at least one of the aspects of embodiments disclosed herein is the realization that it is often difficult to orally administer a drug during emergency situations that may implicate or result in a thromboembolic event. For example, the patient may be experiencing vomiting or otherwise be unable to take the drug orally. Additionally, oral administration of a drug may be undesirable because the drug does not reach the systemic blood stream immediately, thus delaying the important effects of the drug. Even so, due to the first pass effect in the liver and gut, the amount of drug reaching systemic circulation is much less than that administered. Therefore, according to aspects of various embodiments disclosed herein is the realization that an alternative route of administration could avoid these unwanted side-effects.

Various embodiments disclosed herein reflect the novel realization that delivery of a drug by inhalation in the early stages of an emergency situation can provide a fast-acting, effective form of preliminary treatment of certain medical conditions. For example, in some embodiments, upon receiving a complaint of a symptom of a serious thromboembolic event, a patient can be administered, by DPI, a therapeutic amount of a NSAID. The NSAID can address problems associated with or provide an initial treatment for the medical condition.

However, dry powder inhalation of drugs has generally been limited by cough, to dosages of less than a milligram. Recent developments in particle engineering, in particular the development of PulmoSphere™ technology, have enabled the delivery of a larger amount of dry powder to be delivered to the lungs in a single actuation. See David E. Geller, M.D., et al., DEVELOPMENT OF AN INHALED DRY-POWDER FORMULATION OF TOBRAMYCIN USING PULMOSPHERE™ TECHNOLOGY, J Aerosol Med Pulm Drug Deliv. 2011 August; 24(4), pp. 175-82, the entirety of which is incorporated herein by reference. In this publication, a dose of 112 mg tobramycin (in four capsules) was effectively delivered via PulmoSpheres™.

In accordance with some embodiments is the realization that the body includes various particle filters that limit the efficacy of inhaled drugs. For example, the oropharynx tends to prevent passage of particles having a diameter greater than 5 μm. However, in order to reach the alveoli, particles must have a size from about 1 μm to about 5 μm. Accordingly, some embodiments herein disclose the preparation and use of inhalable aspirin using technology similar to PulmoSpheres™ to produce particles with a median geometric diameter of from about 1 μm to about 5 μm, and in some embodiments, from about 1.7 μm to about 2.7 μm.

There has been no single dose use of aspirin by dry powder inhaler to replace the traditional daily use of a NSAID (such as a 81 mg baby aspirin) or emergency use of a NSAID as preventative care for symptoms of a thromboembolic event. Accordingly, some embodiments disclosed herein provide methods for administering a NSAID by dry powder inhalation in an amount less than the dosage of a baby aspirin (i.e., less than 81 mg).

Therefore, in some embodiments, a method for treating disease, e.g., by reducing the risk of a thromboembolic event, can be provided, which comprises administering a NSAID, such as a salicylate, by a DPI or MDI. For example, the method can comprise administering acetylsalicylic acid by a DPI or MDI. The administered dosage can be much less than about 80 mg of acetylsalicylic acid, and can be less than or equal to about 30 mg of acetylsalicylic acid.

For example, according to some embodiments, the dose can be from about 5 mg to about 75 mg. In some embodiments, the dose can be from about 10 mg to about 60 mg. The dose can be from about 15 mg to about 50 mg. Further, in some embodiments, the dose can be from about 20 mg to about 40 mg. In some embodiments, the dose can be about 30 mg. Such dosages can provide a bioequivalent dosage when compared to typical dosages of 81 mg to about 325 mg, while demonstrating few negative side effects.

Thus, in some embodiments, a NSAID, such as aspirin, can be administered by DPI or MDI in a single dose that is much less than a traditional oral dose of aspirin, which can provide an bioequivalent equivalent treatment while tending to avoid the negative side effects associated with some NSAIDs, such as aspirin. Further, systems of administering such treatments are also provided.

The DPI or MDI can have a mouthpiece and an actuation member for making available the NSAID for inhalation by a patient to reduce the risk of the thromboembolic event. For example, the amount of the dose administered can comprise less than about 80 mg of acetylsalicylic acid.

For example, according to some embodiments, a method of reducing the risk of a thromboembolic event is provided and can comprise administering a dose of a nonsteroidal anti-inflammatory drug by a dry powder inhaler. The dose can be effective to reduce a risk of a thromboembolic event in a patient. The dry powder inhaler can have a mouthpiece and an actuation member for making available the dose of the nonsteroidal anti-inflammatory drug for inhalation by the patient to reduce the risk of the thromboembolic event. The amount of the dose administered comprises less than about 80 mg of the nonsteroidal anti-inflammatory drug.

A drug delivery system can also be provided according to some embodiments, for treating a disease, for example, by reducing the risk of a thromboembolic event. The system can comprise a dose of a nonsteroidal anti-inflammatory drug in powder form. The dose can be effective to reduce a risk of a thromboembolic event in a patient. The system can also comprise a dry powder inhaler. The dry powder inhaler can have a mouthpiece, a reservoir for receiving the dose of the nonsteroidal anti-inflammatory drug, and an actuation member for making available the dose of the nonsteroidal anti-inflammatory drug for inhalation by the patient through the mouthpiece. Further, the amount of the dose of the nonsteroidal anti-inflammatory drug comprises less than about 80 mg of the nonsteroidal anti-inflammatory drug.

In some embodiments, the thromboembolic event comprises at least one of myocardial infarction, deep venous thrombosis, pulmonary embolism, or thrombotic stroke. The dose of the nonsteroidal anti-inflammatory drug can be administered as a preliminary treatment in response to a symptom of a thromboembolic event. The nonsteroidal anti-inflammatory drug can comprise aspirin. Further, the dose of the nonsteroidal anti-inflammatory drug can be administered in a single dose.

The dose of the acetylsalicylic acid can comprise an amount from about 5 mg to about 75 mg. The dose of the acetylsalicylic acid can comprise from about 10 mg to about 60 mg. The dose of the acetylsalicylic acid can comprise from about 20 mg to about 40 mg. The dose of the acetylsalicylic acid can comprise from about 25 mg to about 35 mg. Further, the dose of the acetylsalicylic acid can comprise about 30 mg.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

Figure 1:
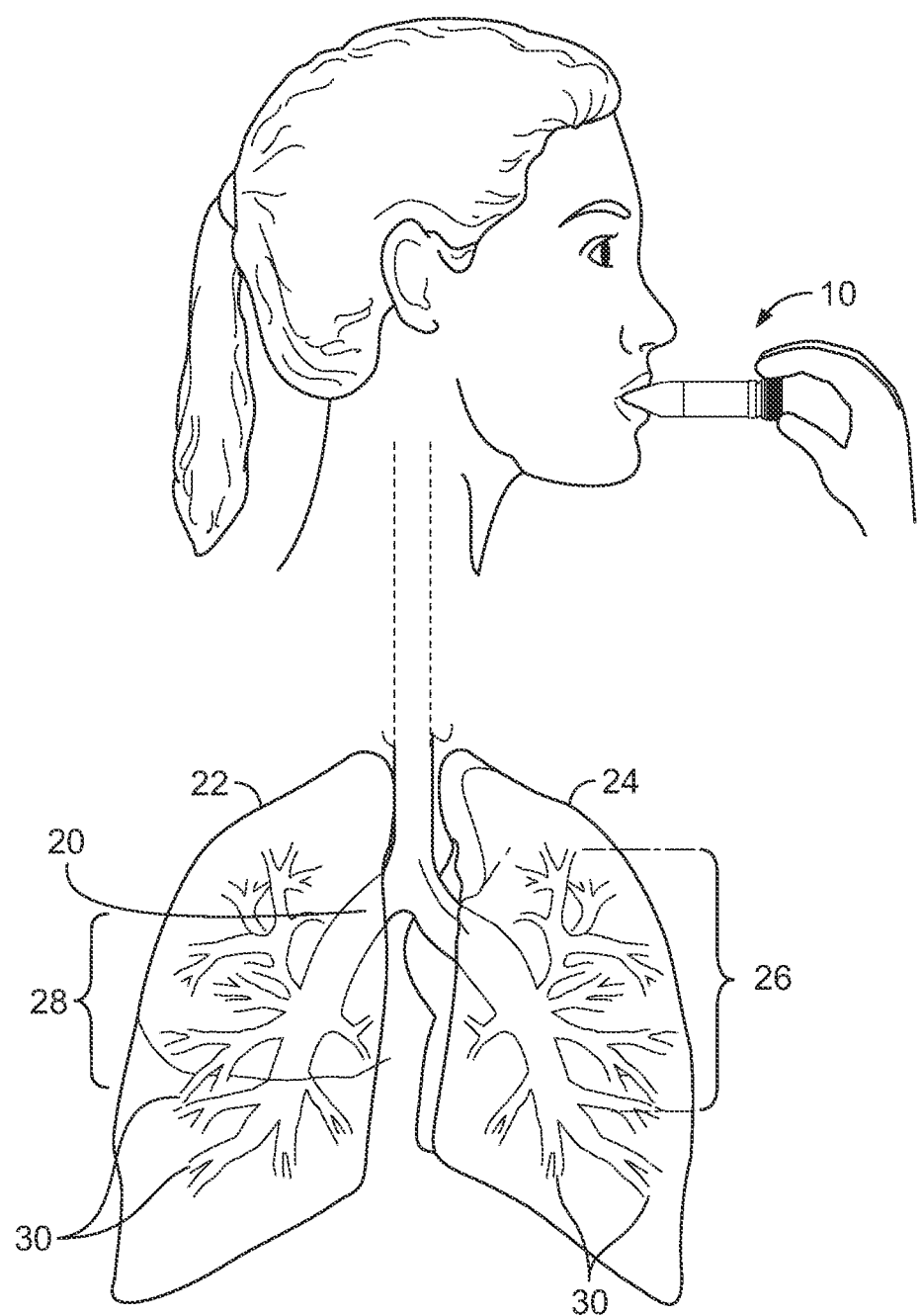
FIG. 1 is a schematic view of a patient using a dry powder inhaler, in accordance with some implementations of the methods and systems disclosed herein.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As discussed above, although NSAIDs, such as aspirin, can provide various beneficial effects and contribute to reducing the likelihood of a thromboembolic event, there may be some drawbacks to their use. Further, the use of NSAIDs, such as aspirin, in a clinical setting has traditionally been limited to oral administration. Oral administration of aspirin, for example, can result in the loss or inactivation of approximately ⅔ of the oral dosage due to the first pass effect in the gut and liver. While one third of the dosage reaches the systemic blood stream and provides the desired effect, the negative side effects created by the full dosage often deter patients from using aspirin on a regular or daily basis.

Further, in many situations, such as in emergencies, oral administration of NSAIDs, such as aspirin, may be inappropriate because it may take too long to be effective. According to at least one aspect of some embodiments disclosed herein is the realization that an alternative administration method and systems can be implemented that utilize a lower dosage and provide a more direct delivery mechanism to the systemic blood stream. Thus, some embodiments disclosed herein allow for the beneficial effects of NSAIDs, such as aspirin, to be achieved on a regular basis and in emergency situations, while minimizing previous drawbacks associated with the use of NSAIDs.

Various studies have determined that aspirin has a significant effect on reducing the risk of myocardial infarction. However, these studies presented inconclusive data on strokes, pulmonary embolism, or deep venous thrombosis. These studies have used aspirin dosages of 325 mg, However, these studies have based their findings on oral administration of aspirin and have not suggested DPI or MDI pathways, which are provided in some embodiments disclosed herein. Further, the administration of aspirin has negative side effects, such as significantly increasing major gastrointestinal and extracranial bleeds by over 50%. This has led some to argue that for preventative treatment, aspirin is of uncertain net value.

Further studies have tested whether the benefits of aspirin could be obtained at low dosages, such as that of baby aspirin (i.e., 81 mg). The Swedish Aspirin Low-dose Trial (SALT) found that a low dose (75 mg/day) of aspirin significantly reduces the risk of stroke or death in patients with cerebrovascular ischaemic events. However, the study also reported gastrointestinal side-effects that included a significant excess of bleeding episodes. A Danish study found that patients receiving aspirin as an antithrombotic agent achieved satisfactory platelet inhibition with 50 mg/day, while the remainder of the patients needed over 50 mg/day. Furthermore, a Dutch TIA Study concluded that aspirin at any dose above 30 mg daily prevents 13% of vascular events, and that there is a need for more efficacious drugs. There continues to be significant debate about the efficacy of very low doses of aspirin. However, no study or teaching has been provided regarding the administration of aspirin by DPI or MDI at very low doses.

Additionally, the applicant notes that although inhaled dry powder formulations of aspirin have been developed, reports have stated that the formulation was not clinically feasible because it is difficult to meet the high dosage requirements of aspirin (~80 mg/day for low-dose prevention of coronary events and stroke, and at least 300 mg/day for pain or fever relief) via pulmonary delivery of dry powders.

In addition, these reports recognize that adverse effects of dry powder on the lungs, such as coughing, cannot be avoided unless the doses are less than a few tenths of a milligram in a single breath. Thus, prior teachings suggest that higher dosage requirements of aspirin would be impossible to meet using DPI. Finally, some have taught that there is a higher incidence of aspirin intolerance in asthmatic patients when aspirin is delivered by inhalation than orally.

In yet another study, the authors noted that use of nanoparticulate drugs for dry powder inhaler (DPI) delivery is not straightforward. Direct inhalation of nanoparticulate drugs was infeasible due to their small size. The nanometer size leads to the nanoparticulate drugs being predominantly exhaled from the lungs, without any deposition taking place. Moreover, a severe aggregation problem arising from the small size makes their physical handling difficult for DPI delivery. Accordingly, "large hollow carrier particles" of nanoparticulate drugs has been developed for pulmonary delivery of some drugs. See Hadinoto et al., *Drug Release Study Of Large Hollow Nanoparticulate Aggregates Carrier Particles For Pulmonary Delivery*, International Journal of Pharmaceutics 341 (2007) 195-20, the entirety of which is incorporated by reference herein.

In the Hadinoto study, the authors used aspirin as a model for "lowly water-soluble" drugs. The authors acknowledged that "with regard to the aspirin, the nanoparticulate polymer delivery method is not the most suitable method of delivery due to the high dosage requirement of aspirin (~300 mg/day)," and overall, the aim of the study was to identify key facets in the formulation of the large hollow nanoparticulate aggregates. See id.

In some embodiments of the inventions disclosed herein, methods and systems are provided for treating a disease, for example, by reducing the risk of a thromboembolic event by administration of a very low amount of a NSAID, such as a low dose of aspirin, by DPI or MDI. The dose can be much less than that of a baby aspirin (less than 81 mg). For example, the dose can be from about 5 mg to about 75 mg. In some embodiments, the dose can be from about 8 mg to about 60 mg. The dose can be from about 10 mg to about 50 mg. Further, in some embodiments, the dose can be from about 15 mg to about 40 mg. In some embodiments, the dose can be about 18 mg or about 20 mg. Such dosages can provide a bioequivalent dosage when compared to typical dosages of 81 mg to about 325 mg, while demonstrating few negative side effects.

Referring to FIG. 1, in a dry powder inhalation technique, a patient can use a dry powder inhaler 10 to inhale a powder formulation of a drug, such as a NSAID. The dose is effective to reduce a risk of a thromboembolic event in the patient. An aspect of some embodiments is the realization that because the lung is an efficient filter, it generally only permits particles having a size of less than 5 μm. For example, after the drug enters the main stem bronchus 20, the drug will enter each lung 22, 24. The drug can then pass through the bronchial trees 26, 28 until reaching the individual alveoli 30 in the lungs 22, 24, which are exceedingly numerous, as discussed below. Of each long Thus, the dry powder inhaler 10 can allow the patient to self administer a dosage of particles having a size of from about 1 μm and about 5 μm. In some embodiments, the particle size can be from about 2 μm to about 4 μm.

According to some embodiments, various types of inhalers can be used to provide the drug using a DPI or MDI delivery system. The dose administered can be effective to reduce a risk of a thromboembolic event in a patient.

For example, the dry powder inhaler 10 can comprise a mouthpiece, a reservoir for receiving the NSAID, and an actuation member for making available the NSAID for inhalation by a patient through the mouthpiece.

For example, FIGS. 2A-2F illustrate a DPI delivery device 100 having a mouthpiece 102 and a drug compartment 104. The drug compartment 104 can be inserted into an inhaler body cavity 110.

Figure 2A:
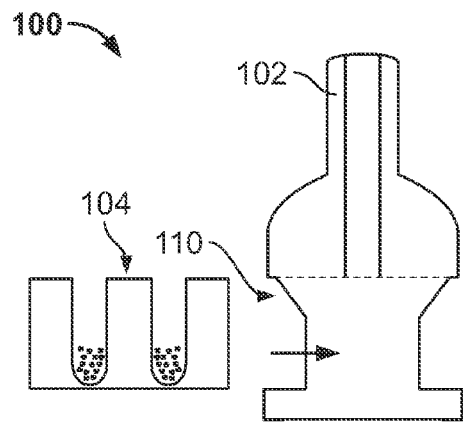
FIGS. 2A-F illustrate usages and a configuration of a dry powder inhaler, according to some embodiments.
Figure 2B:
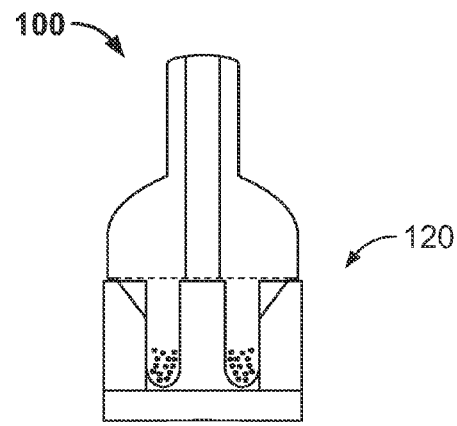
Figure 2C:
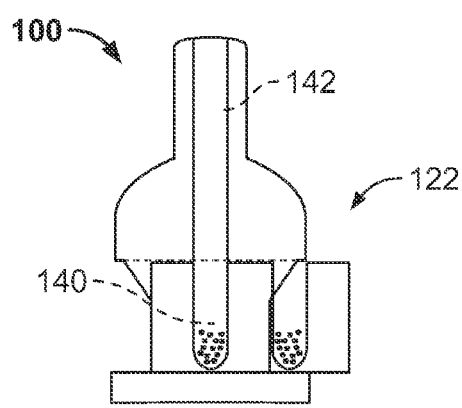
Figure 2D:
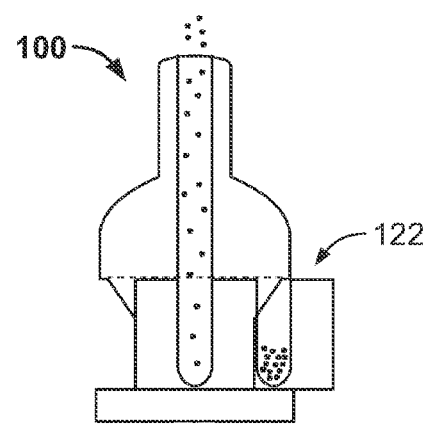

For example, as shown in FIG. 2B, the drug compartment 104 can be inserted into the body cavity 110 into a stowed position 120 for storage purposes. However, the drug compartment 104 can also be moved to a first position 122, shown in FIG. 2C, in which a first receptacle 140 of the drug compartment 104 is aligned with a mouthpiece airway 142. In this first position 122, the drug contained in the first receptacle 140 can be delivered through the mouthpiece airway 142 to be inhaled by the patient, as illustrated in FIG. 2D.

Figure 2E:
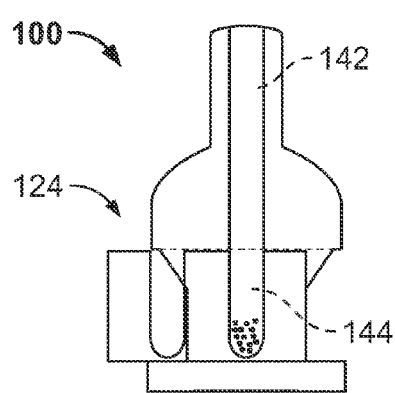
Figure 2F:
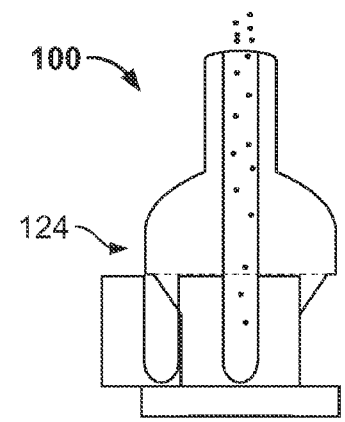

Additionally, as shown in FIG. 2E, the drug compartment 104 can be moved to a second position 124 in which a second receptacle 144 is aligned with the mouthpiece airway 142. Thus position, the drug contained in the second receptacle 144 can be inhaled by the patient, as illustrated in FIG. 2F.

In some embodiments, NSAIDs can be used in various methods and systems. In some embodiments, NSAIDs can include salicylates, i.e., the salts and esters of salicylic acid, that have anti-platelet action. Further, NSAIDs can also include one or more of the following:

Aspirin (Aspirin is a brand name; the chemical is called acetylsalicylic acid)
Celecoxib (Celebrex)
Dexdetoprofen (Keral)
Diclofenac (Voltaren, Cataflam, Voltaren-XR)
Diflunisal (Dolobid)
Etodolac (Lodine, Lodine XL)
Etoricoxib (Algix)
Fenoprofen (Fenopron, Nalfron)
Firocoxib (Equioxx, Previcox)
Flurbiprofen (Urbifen, Ansaid, Flurwood, Froben)
Ibuprofen (Advil, Brufen, Motrin, Nurofen, Medipren, Nuprin)
Indomethacin (Indocin, Indocin SR, Indocin IV)
Ketoprofen (Actron, Orudis, Oruvail, Ketoflam)
Ketorolac (Toradol, Sprix, Toradol IV/IM, Toradol IM)
Licofelone (under development)
Lornoxicam (Xefo)
Loxoprofen (Loxonin, Loxomac, Oxeno)
Lumiracoxib (Prexige)
Meclofenamic acid (Meclomen)
Mefenamic acid (Ponstel)
Meloxicam (Movalis, Melox, Recoxa, Mobic)
Nabumetone (Relafen)
Naproxen (Aleve, Anaprox, Midol Extended Relief, Naprosyn, Naprelan)
Nimesulide (Sulide, Nimalox, Mesulid)
Oxaporozin (Daypro, Dayrun, Duraprox)
Parecoxib (Dynastat)
Piroxicam (Feldene)
Rofecoxib (Vioxx, Ceoxx, Ceeoxx)
Salsalate (Mono-Gesic, Salflex, Disalcid, Salsitab)
Sulindac (Clinoril)
Tenoxicam (Mobiflex)
Tolfenamic acid (Clotam Rapid, Tufnil)
Valdecoxib (Bextra)

Other alternatives can also be used instead of a NSAID in some methods or systems disclosed herein. Such alternatives include as Plavix (clopidogrel), COX-2 inhibitors, other remedies such as Nattokinase (an enzyme (EC 3.4.21.62, extracted and purified from a Japanese food called nattē). Further, other drugs that provide different beneficial effects, such as being effective to reduce a risk of a thromboembolic event in a patient, can also be used in some embodiments. Thus, the discussion of methods and systems shall apply generally to these various alternatives, although for discussion purposes, the present disclosure often refers to aspirin. It is contemplated that the methods, effects, pharmacokinetic data, and other considerations relating to aspirin can be equally applied to other NSAIDs, according to some embodiments.

Through some of the embodiments disclosed herein, the applicant notes have overcome the challenges acknowledged by prior teachings. In particular, the applicant notes have recognized that when a drug is inhaled into the lungs, the drug can be dispersed toward the alveoli. Although alveoli primarily function to exchange carbon dioxide for oxygen, alveoli also produce enzymes. Thus, inhaled substances, such as pathogens, drugs, or other chemicals, may be processed at the alveoli.

An alveolus comprises a network of elastic fibers and capillaries, resembling a woven sphere on its outer surface. The capillaries function to carry oxygen depleted blood toward the lungs and oxygen rich blood away from the lungs, via the pulmonary artery and the pulmonary vein. The interior of each alveoli comprises a thin tissue known as an alveolar lining or epithelium. Alveolar epithelium is made of two distinct types of cells, known as flat type I and type II. Flat type I cells cover most of the surface area of the epithelium and are closely spaced, allowing only small molecules to pass therebetween, such as oxygen and carbon dioxide. Type II alveolar cells aid in producing the pulmonary surfactant used in gas exchange. Further, the alveolar epithelium also comprises macrophages, which assist in disposing of fine particulate foreign matter such as dust, tar, and pathogens. Despite the diminutive size of the alveoli (being only approximately 250 μm), because an adult can have between 200 million and 400 million alveoli, the alveolar respiratory surface area can be from approximately 1,400 to about 1,600 square feet.

According to some embodiments disclosed herein, absorption of NSAIDs administered by DPI or MDI through the pulmonary capillaries and epithelium can provide an immediately effective treatment to address symptoms of thromboembolic events. One of the novel realizations of some embodiments is that the substantial first pass effect produced by oral administration of NSAIDs, such as aspirin, can be avoided through administration by dry powder inhaler. In addition, there has hitherto been no teaching or suggestion regarding the pharmacokinetics of dry powder delivery of a NSAID, such as aspirin, and the possible metabolism or inactivation of the drug as it encounters the endothelial tissue of the pulmonary capillaries.

The delivery of a NSAID by DPI or MDI is a complex and unpredictable technological area that has not provided straightforward or expected results to a person of skill in the art. Accordingly, there has been no reason for a person of skill to believe that a combination of prior systems or treatment methods could produce the embodiments disclosed herein. For example, some embodiments herein recognize an unexpected result that as a drug crosses the endothelium of pulmonary arteries and alveoli, the first pass effect is minimized and results in a much lower rate of the activation of the drug than in other drug delivery pathways.

The endothelium of the pulmonary capillaries serve as a barrier by selectively allowing materials to exit or enter the bloodstream. It would be expected that aspirin would be inactivated in the pulmonary capillaries, which are lined by endothelial cells. The endothelial cells are extremely metabolically active. Thus, a person of skill would expect that aspirin would be inactivated by the endothelium of the pulmonary capillaries. However, according to some embodiments disclosed herein, it is contemplated that as the powdered drug encounters the endothelium, the endothelium can metabolize or activate a much smaller portion of the powdered drug compared to the metabolism provided by the gut and liver. For example, after being transformed in the stomach to salicylic acid, as much as 80% of the salicylic acid is metabolized in the liver. Thus, only a small minority of the salicylic acid is bioavailable to the systemic blood stream.

However, it is contemplated that a vast majority of the salicylic acid metabolized from the inhaled aspirin powder will be bioavailable to the systemic blood stream. Thus, a dose of much less than that of a baby aspirin (less than 81 mg) can be provided by dry powder inhalation. This can provide a much lower dosage while providing a bioequivalent dosage.

Further, in accordance an aspect of some embodiments, it is contemplated that an analogous first pass effect may be experienced in the endothelium of the pulmonary capillaries. Accordingly, with regard to the provision of an inhaled dosage that is the bioequivalent of a baby aspirin administered orally, the inhaled dosage should account for some first pass effect experience through the endothelium of the pulmonary capillaries.

In accordance with some embodiments, the first pass effect through the endothelium of the pulmonary capillaries can be a minimum, which provides little overall effect on the inhaled dosage.

For example, the dose of a NSAID, such as aspirin, can be less than about 80 mg. In some embodiments, the dose of a NSAID can be from about 5 mg to about 75 mg. In some embodiments, the dose of a NSAID can be from about 10 mg to about 60 mg. In some embodiments, the dose of a NSAID can be from about 20 mg to about 40 mg. In some embodiments, the dose of a NSAID can be from about 25 mg to about 35 mg. In some embodiments, the dose of a NSAID can be about 30 mg. In some embodiments, the dose of a NSAID can be about 30 mg. Further, the NSAID can be from about 5 mg and about 20 mg. The NSAID can be about However, it is also contemplated that in some embodiments, the first pass effect through the endothelium of the pulmonary capillaries can be entirely negligible. Thus, the amount of the inhaled dosage need not be adjusted to compensate for first pass effect through the pulmonary capillaries.

Therefore, some embodiments recognize the unexpected result that even extremely low doses of aspirin (and likely other NSAIDs) can provide a significant therapeutic effect while providing to minimal or inconsequential side effects. For example, doses as low as 5 mg can be effective in reducing the risk of a thromboembolic event. Accordingly, the net benefits increased dramatically at significantly lower doses, according to some embodiments. These results and outcomes are unexpected given the complex and unpredictable nature of drug interactions in the body, drug delivery pathways, and microscopic drug structures. Finally, no teachings or other prior references disclose a system or process for achieving therapeutically beneficial results while substantially avoiding any negative side effects using DPI or MDI drug delivery mechanisms with microscopic NSAIDs.

In accordance with some embodiments, the dry powder administration of the NSAID, such as a salicylate like acetylsalicylic acid, can comprise particles having a size of from about 1 μm to about 5 μm, as discussed above. The particles can be highly porous and demonstrate a sponge-like morphology or be a component of a carrier particle. The particles can also demonstrate a spheroidal shape, by which the shape and porous surface can serve to decrease the area of contact between particles, thereby leading to less particle agglomeration and more effective distribution throughout the lung. Dry powder technologies, such as PulmoSphere™, may be implemented in embodiments of the methods and systems disclosed herein.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A method of reducing risk of a thromboembolic event, the method consisting of the step of administering through oral inhalation to a patient in an emergency a single dose of acetylsalicylic acid formulated as a dry powder comprising dry particles, the dose effective to reduce the risk of the thromboembolic event in the patient, by a dry powder inhaler, the dry powder inhaler having a mouthpiece and an actuation member for making available the dose of the acetylsalicylic acid for inhalation by the patient to reduce the risk of the thromboembolic event, wherein the amount of the dose administered to the patient in the emergency comprises less than 60 mg of acetylsalicylic acid, and wherein the particles have a median geometric diameter ranging from 1 μm to about 5 μm.

2. The method of claim 1, wherein the dose of the acetylsalicylic acid comprises an amount from about 5 mg to about 60 mg.

3. The method of claim 1, wherein the dose of the acetylsalicylic acid comprises from about 8 mg to about 60 mg.

4. The method of claim 1, wherein the dose of the acetylsalicylic acid comprises from about 10 mg to about 40 mg.

5. The method of claim 1, wherein the dose of the acetylsalicylic acid comprises from about 15 mg to about 30 mg.

6. The method of claim 1, wherein the dose of the acetylsalicylic acid comprises about 20 mg.

7. The method of claim 1, wherein the dose of the acetylsalicylic acid comprises about 18 mg.

8. The method of claim 1, wherein the dose of the acetylsalicylic acid is administered as a preliminary treatment in response to a symptom of a thromboembolic event.

9. A drug delivery system for reducing risk of a thromboembolic event, the system comprising:
a single dose of acetylsalicylic acid in powder form comprising dry particles, the dose effective to reduce the risk of the thromboembolic event in a patient in an emergency;
a dry powder inhaler for oral inhalation, the dry powder inhaler having a mouthpiece, a reservoir for receiving the dose of acetylsalicylic acid, and an actuation member for making available the dose of the acetylsalicylic acid for inhalation by the patient through the mouthpiece,
wherein the dose of acetylsalicylic acid administered to the patient in the emergency comprises less than 60 mg of acetylsalicylic acid, and wherein the particles have a median geometric diameter ranging from about 1 μm to about 5 μm.

10. The system of claim 9, wherein the dose of the acetylsalicylic acid comprises an amount from about 5 mg to about 60 mg.

11. The system of claim 9, wherein the dose of the acetylsalicylic acid comprises from about 8 mg to about 60 mg.

12. The system of claim 9, wherein the dose of the acetylsalicylic acid comprises from about 10 mg to about 40 mg.

13. The system of claim 9, wherein the dose of the acetylsalicylic acid comprises from about 15 mg to about 30 mg.

14. The system of claim 9, wherein the dose of the acetylsalicylic acid comprises about 20 mg.

15. The system of claim 9, wherein the dose of the acetylsalicylic acid comprises about 18 mg.

\* \* \* \* \*